United States Patent [19]

Selinger

[11] Patent Number: 5,747,752
[45] Date of Patent: May 5, 1998

[54] STETHOSCOPE WITH DISPOSABLE CHESTPIECE

[75] Inventor: Irwin Selinger, Old Westbury, N.Y.

[73] Assignee: Graham-Field, Inc., Hauppauge, N.Y.

[21] Appl. No.: 792,582

[22] Filed: Jan. 30, 1997

[51] Int. Cl.$^6$ .................................................. A61B 7/02
[52] U.S. Cl. ................................................ 181/131; 181/137
[58] Field of Search .................................. 181/131, 137; 381/67; 128/715

[56] References Cited

U.S. PATENT DOCUMENTS

| | | | |
|---|---|---|---|
| 2,233,087 | 2/1941 | Tynan | 181/131 |
| 3,999,625 | 12/1976 | Pickett et al. | 181/131 |
| 4,867,268 | 9/1989 | Ulert | 181/137 |
| 4,997,055 | 3/1991 | Grady | 181/131 |

*Primary Examiner*—Khanh Dang
*Attorney, Agent, or Firm*—Bauer & Schaffer

[57] ABSTRACT

A removable and disposable chestpiece for a stethoscope. The chestpiece comprises a unitary disk-like chamber have opposed walls connected by a peripheral wall. One of the opposed walls is provided with a central opening. The head of the stethoscope is provided with an extending skirt which fits into the hole of the chestpiece.

4 Claims, 1 Drawing Sheet

STETHOSCOPE WITH DISPOSABLE CHESTPIECE

BACKGROUND OF THE INVENTION

The present invention relates to an improvement in the construction of stethoscopes and, in particular, to a disposable chestpiece for stethoscopes.

Conventional stethoscopes consist of a chestpiece or bell connected at the end of a sound tube whereby the heartbeat is transmitted to the ear of the physician. The chestpiece is permanently affixed to a valve system which provides a controlled connection to the tube. As such, the chestpiece ia an integral and fixed part of the sound tube. It cannot be easily removed nor cleaned, requiring the physician to manually clean the chestpiece by hand.

The importance of sterile instruments to insure safety has been common knowledge in the medical field for many years. Sterile instruments are vital to prevent the spread of germs and disease from one patient to another. As such, physicians have be forced to clean the chestpiece by hand, in an attempt to sterilize the stethoscope. This process is both time consuming and not fully effective in insuring a sterile instrument. If the chestpiece could be removed and thus easily cleaned and/or discarded so that it can be replaced after each use with a new and/or used, but sterile chestpiece, the chance of spreading germs from one patient to another would be greatly reduced.

It is therefore, the object of the present invention to provide a removable chestpiece for stethoscopes.

It is a further object to provide a disposable chestpiece, allowing the physician to remove and dispose of the chestpiece after each use.

It is a further object of the present invention to provide a inexpensive disposable chestpiece to be used with a conventional stethoscope.

These objects, together with other objects and advantages, will be apparent from the following disclosure of the present invention.

SUMMARY OF THE INVENTION

Briefly, in accordance with the present invention, a stethoscope having a removable, cleansible and/or disposable chestpiece for a stethoscope is provided. The chestpiece is formed in the shape of a hollow disk body defining a sound chamber. The body is provided with a centrally located circular orifice in one of its walls containing depending tabs that allow the chestpiece to be resiliently, yet selectively, affixed about the end of the sound tube or the control valve.

Preferably, the disk-like body has a pair of parallel circular walls separated by a continuous peripheral side wall. One wall of the chestpiece is provided with the centrally located orifice that is slightly larger in diameter than the circular protrusion provided on end of the stethoscope, allowing the chestpiece to be snugly secured about the protrusion. The other wall is smooth so as to be placable against the surface of the patient's skin. The orifice is defined with tabs that depend slightly into the chestpiece. These tabs provide the necessary frictional force to hold the chestpiece securely around the circular protrusion of the sound tube.

Full details of the present invention are set forth in the following description and illustrated in the accompanying drawings.

DESCRIPTION OF THE INVENTION

Figure 1:
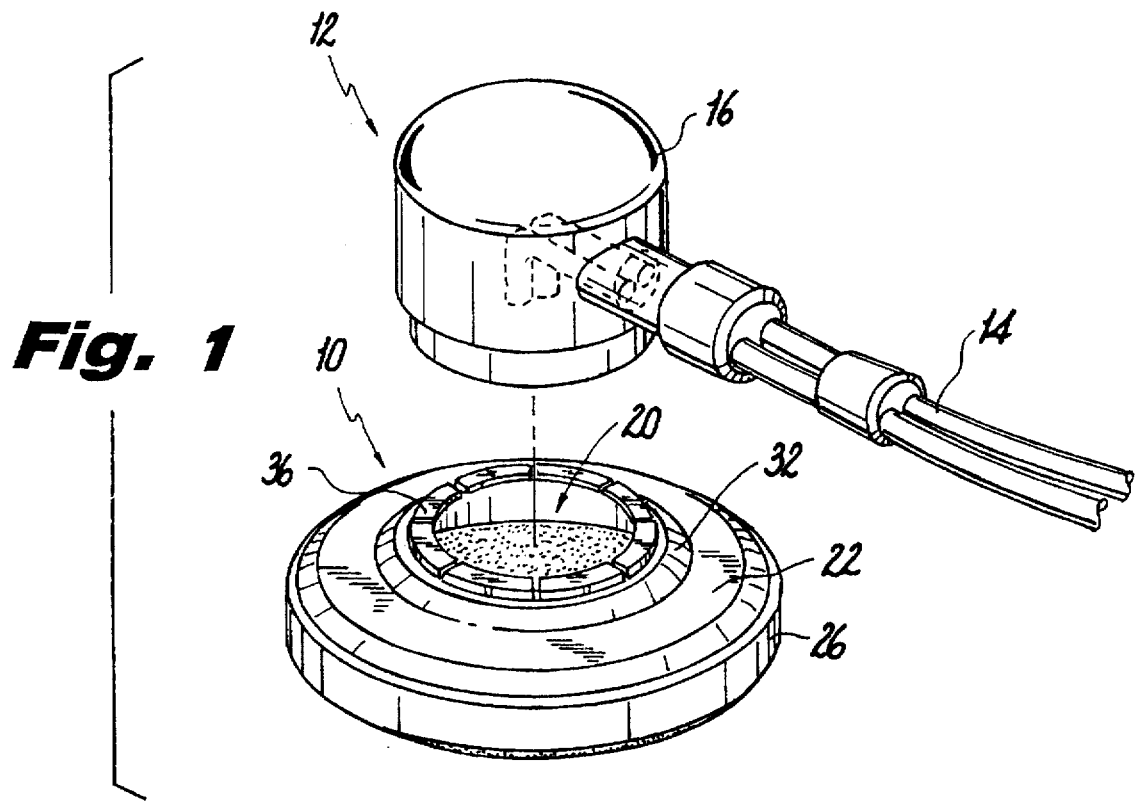
FIG. 1 is a exploded perspective view of the body of the stethoscope and the removable chestpiece.

As seen in the Figures, the chestpiece or bell of the present invention generally depicted by the numeral 10 is illustrated in combination with a stethoscope, generally depicted by the numeral 12. The stethoscope comprises a pair of flexible auscultatory or ear tubes 14 and a head 16 in which the tubes 14 jointly terminate. The free end of each tube is provided with an earpiece (not shown).

Extending from the head 16 is a hollow cylindrical skirt 18, over which the chestpiece 10 fits. The chestpiece has a central hole 20 into which the skirt 18 fits snugly to prevent air or sound loss and to which the chestpiece is removably held.

Figure 2:
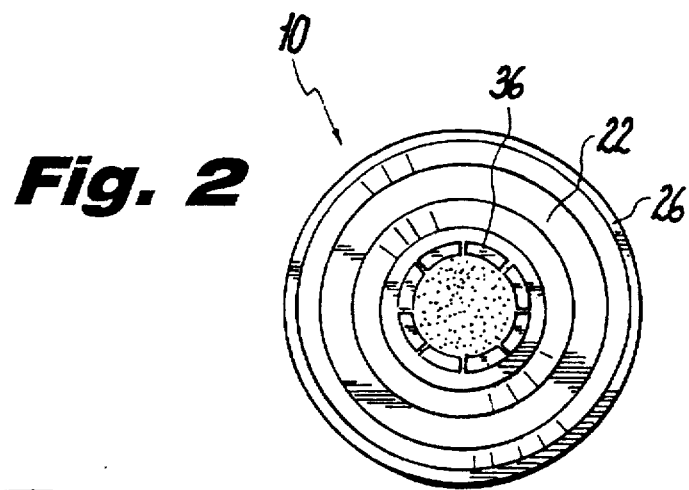
FIG. 2 is a top plain view of the chestpiece.
Figure 3:
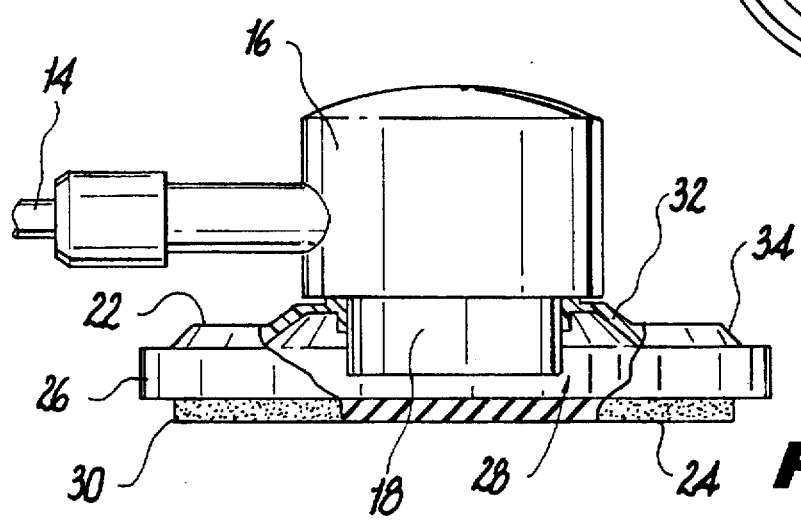
FIG. 3 is a side elevational view of the chestpiece partially sectioned to show its interior.

The chestpiece 10, as can be seen in FIGS. 2–4, comprises a unitary body formed of a pair of spaced generally parallel disk-like faces 22 and 24 joined by a circumferential wall 26, so as to define a hollow acoustic chamber 28 or sound box. The bottom face 24, acting as the diaphragm of the chestpiece, has an enlarged flat surface adapted to be applied to the patient in use, and is provided with a shallow peripheral bevel 30 reducing damping as a result of its connection to the circumferential wall 26. The upper face 22 is formed step-like with two peripheral bevels 32 and 34 to create a dome shape adding some rigidity to the face 22. The circumferential wall 26 may be made somewhat thicker than the bottom wall to maintain the shape and structure of the chestpiece when applied to a patient's body. At the center of the face 22, there is formed a hole 20 into which the cylindrical skirt 18 is inserted. Surrounding the hole 20 is a series of spring-like tabs 36 that descend from the inner edge of the connection hole into the acoustic chamber. The tabs 36 act to cooperatively grasp the surface of the skirt 18 and provide the necessary frictional force to hold the chestpiece in place without a more permanent or fixed fastening. If desired, the skirt 18 can be formed with a circular bead to grasp the tabs 36. Ideally, the tabs are approximately ³⁄₁₆" in length.

The chestpiece is preferably constructed of plastic, thereby providing an inexpensive material, which can be discarded after each use. It is preferably molded in one piece so as to be completely unitary and is symmetrical about its center and has walls, each of which is of uniform thickness although respectively of different thickness. Plastic also has the benefit of having a low thermal conductivity which will improve the comfort level of the patient by avoiding the chill often associated with conventional metal stethoscopes.

As will be apparent from the foregoing, the present invention provides a chestpiece which is removable but easily affixed for security during use. The chestpiece may be removed for cleansing, sterilization and/or it may be disposed of and replaced with a new chestpiece. The disposability of the chestpiece permits the preservation of truly sterile conditions by allowing the physician to dispose of the chestpiece in the field or under emergency conditions, where cleansing and sterilization equipment are unavailable.

The size of the chestpiece, itself, may vary in conformity to current practice, where both small and large chestpieces or bell pieces are in use. Various sizes may be provided to the physician who will select the desired size. Similarly, the chestpiece will be formed so the diameter of the hole, by which the chestpiece is connected to the skirt of the stethoscope, will conform to the skirt. Thus, a variety of sizes may be provided; the actual number of sizes will, of course, be minimized by the existence of the spring tabs.

Actually, the construction of the stethoscope tubes and earpiece will not be effected, and they will remain the same as now formed. The head construction will also not be changed, except for the formation of the extending skirt.

Various modifications have been suggested herein. Other changes and modifications will be apparent to those skilled in this art. It is therefore intended that the present disclosure be taken as illustrative only and not as limiting of the invention.

What is claimed is:

1. A stethoscope having a pair of elongated flexible ear tubes, having a head at one end and a chestpiece connected to said head, said chestpiece comprising a unitary body defining a sound chamber having at least one pair of opposed spaced walls connected by a peripheral wall of treater rigidity than said pair of walls, and one of said walls being formed as a diaphragm, the other of said walls having hole therein, said hole and said head having cooperating means for removably attaching said chestpiece to said head.

2. The stethoscope according to claim 1, wherein said chestpiece is integrally molded of plastic.

3. The stethoscope according to claim 1, wherein the cooperating attaching means comprises a cylindrical skirt extending from the head of said stethoscope into the hole in said chestpiece.

4. The stethoscope according to claim 3, wherein the cooperating attaching means comprises a plurality of spring-like tabs ringing said hole and coacting with the skirt of said head.

* * * * *

UNITED STATES PATENT AND TRADEMARK OFFICE
CERTIFICATE OF CORRECTION

PATENT NO. : 5,747,752
DATED : May 5, 1998
INVENTOR(S) : Irwin Selinger

It is certified that error appears in the above-indentified patent and that said Letters Patent is hereby corrected as shown below:

Claim 1, Column 4, line 3: change "treater" to --greater--.

Signed and Sealed this

Seventh Day of July, 1998

Attest:

BRUCE LEHMAN

Attesting Officer          Commissioner of Patents and Trademarks